United States Patent
Yagi et al.

(10) Patent No.: US 10,074,933 B2
(45) Date of Patent: Sep. 11, 2018

(54) FOR DIAGNOSTIC ULTRASOUND PROBE CABLE TENSILE STRENGTH BY FOLDING THE SHEILD BACK AND HOLDING BY TWO RINGS

(71) Applicant: HITACHI, LTD., Chiyoda-ku, Tokyo (JP)

(72) Inventors: Tomoyuki Yagi, Nagareyama (JP); Gen Shiina, Higashimurayama (JP); Hakaru Matsui, Hitachi (JP)

(73) Assignee: HITACHI, LTD., Tokyo (JP)

( * ) Notice: Subject to any disclaimer, the term of this patent is extended or adjusted under 35 U.S.C. 154(b) by 871 days.

(21) Appl. No.: 14/389,541

(22) PCT Filed: Mar. 14, 2013

(86) PCT No.: PCT/JP2013/057199
§ 371 (c)(1),
(2) Date: Sep. 30, 2014

(87) PCT Pub. No.: WO2013/146297
PCT Pub. Date: Oct. 3, 2013

(65) Prior Publication Data
US 2015/0303616 A1 Oct. 22, 2015

(30) Foreign Application Priority Data
Mar. 30, 2012 (JP) .................................. 2012-081731

(51) Int. Cl.
*A61B 8/00* (2006.01)
*H01R 13/58* (2006.01)
(Continued)

(52) U.S. Cl.
CPC ....... *H01R 13/5845* (2013.01); *A61B 8/4444* (2013.01); *A61B 8/56* (2013.01);
(Continued)

(58) Field of Classification Search
CPC ..................................... Y10S 439/00-439/957
See application file for complete search history.

(56) References Cited

U.S. PATENT DOCUMENTS

| | | | | |
|---|---|---|---|---|
| 4,026,628 A | * | 5/1977 | Duffner | H01R 9/032 439/585 |
| 4,902,249 A | | 2/1990 | Morishita et al. | |

(Continued)

FOREIGN PATENT DOCUMENTS

| | | |
|---|---|---|
| JP | U 60-17041 | 2/1985 |
| JP | U 1-115182 | 8/1989 |

(Continued)

OTHER PUBLICATIONS

Apr. 9, 2013 International Search Report issued in International Patent Application No. PCT/JP2013/057199.

*Primary Examiner* — Serkan Akar
(74) *Attorney, Agent, or Firm* — Oliff PLC

(57) ABSTRACT

An ultrasound probe according to the present invention includes: a main body section including a plurality of transducers configured to send and receive an ultrasonic wave to and from an inside of a diagnosing object; a cable including a plurality of signal lines connected to the plurality of transducers, and a sheath configured to cover the plurality of signal lines; a connector section configured to connect the cable to an ultrasound diagnostic apparatus; and a bush including a through hole where the cable is passed, configured to fix the cable passed through the through hole together with the sheath that is folded back, and including a fixed portion fixed, in place, to the connector section.

12 Claims, 15 Drawing Sheets

(51) Int. Cl.
*H01B 3/44* (2006.01)
*H01B 3/46* (2006.01)
*H01R 11/18* (2006.01)
*H02G 3/04* (2006.01)
*A61B 8/12* (2006.01)

(52) U.S. Cl.
CPC ............... H01B 3/445 (2013.01); H01B 3/46 (2013.01); H01R 11/18 (2013.01); H02G 3/0462 (2013.01); *A61B 8/12* (2013.01); *A61B 8/4494* (2013.01); *A61B 2562/222* (2013.01); *A61B 2562/225* (2013.01)

(56) References Cited

U.S. PATENT DOCUMENTS

| | | | |
|---|---|---|---|
| 4,929,189 A | | 5/1990 | Sekiguchi |
| 7,942,695 B1 * | | 5/2011 | Lu ........................ H01R 13/111 439/578 |

FOREIGN PATENT DOCUMENTS

| | | |
|---|---|---|
| JP | U 1-177883 | 12/1989 |
| JP | U 2-143913 | 12/1990 |
| JP | U 3075662 | 2/2001 |
| JP | A 2011-10664 | 1/2011 |
| JP | A 2011-152326 | 8/2011 |
| KR | 10-2007-0062758 | 6/2007 |

\* cited by examiner

FOR DIAGNOSTIC ULTRASOUND PROBE CABLE TENSILE STRENGTH BY FOLDING THE SHEILD BACK AND HOLDING BY TWO RINGS

TECHNICAL FIELD

The present invention relates to an ultrasound probe or an ultrasound probe cable, and more particularly, to a cable fixing structure for connecting an ultrasound probe to a main body of an ultrasound diagnostic apparatus.

BACKGROUND ART

An ultrasound diagnostic apparatus is an apparatus which sends ultrasonic waves to a diagnosing object and receives reflected waves from an inner portion of the diagnosing object with an ultrasound probe contacting a surface of the diagnosing object, displays biological information of each region in the diagnosing object by means of an image, such as a cross-section region image, based on reflected echo signals as the received signals, and uses the biological information for diagnosis (see Patent Literature 1).

The ultrasound probe has a configuration in which a plurality of transducers configured to send the ultrasonic waves, and receive the reflected waves from the inner portion of the diagnosing object are lined up and arranged on an ultrasonic wave sending/receiving surface. Normally, the ultrasound probe is detachably connected to a main body (referred to as an apparatus main body below) of the ultrasound diagnostic apparatus via a cable. The cable is fixed to a connector case of a connector section, which serves as a connection interface with the apparatus main body, by a bush, and connected to a connector target section of the apparatus main body. The cable connected to the apparatus main body transmits various signals between the plurality of transducers of the ultrasound probe and the apparatus main body configured to control the transducers.

Therefore, to perform stable signal transmission, the cable needs to be surely fixed to the connector case via the bush, and connected to the apparatus main body even when receiving a stress while a user is operating the ultrasound probe. For example, it is defined in IEC60601-1, clause 56 (second edition) that a cable has a strength to be able to withstand a reference tensile stress (100[N]).

CITATION LIST

Patent Literature

Patent Literature 1: JP-A-2011-10664

SUMMARY OF INVENTION

Technical Problem

In the ultrasound diagnostic apparatus, a reduction in size and weight of the apparatus main body is being promoted, and a hand-carry type apparatus is beginning to be used. In the hand-carry type ultrasound diagnostic apparatus, it is necessary to achieve a reduction in size and weight of the connector section as well as the reduction in size and weight of the apparatus main body.

Therefore, to achieve the reduction in size and weight of the connector section, it is necessary to maintain a tensile strength of the cable meeting the IEC standard while keeping a cable fixing space in the connector case to the minimum necessary.

The present invention has been made in view of the above circumstances, and an object to be attained thereof is to achieve space saving of a space for fixing a cable of an ultrasound probe, and improvement of a tensile strength of the cable.

Solution to Problem

To attain the above object, an ultrasound probe of the present invention includes: a main body section including a plurality of transducers configured to send and receive an ultrasonic wave to and from an inside of a diagnosing object; a cable including a plurality of signal lines connected to the plurality of transducers, and a sheath configured to cover the plurality of signal lines; a connector section configured to connect the cable to an ultrasound diagnostic apparatus; and a bush including a through hole where the cable is passed, configured to fix the cable passed through the through hole together with the sheath that is folded back, and including a fixed portion fixed, in place, to the connector section.

Also, an ultrasound probe cable of the present invention includes: a plurality of signal lines connected to a plurality of transducers; a sheath configured to cover the plurality of signal lines; and a bush including a through hole where the plurality of signal lines are passed, and configured to fix the plurality of signal lines passed through the through hole together with the sheath that is folded back.

Advantageous Effects of Invention

In accordance with the ultrasound probe or the ultrasound probe cable of the present invention, space saving of a space for fixing the cable, and improvement of a tensile strength of the cable can be achieved.

BRIEF DESCRIPTION OF DRAWINGS

FIG. 3(a) illustrates a sectional view; FIG. 3(b) illustrates a plan view; and FIG. 3(c) illustrates a state in which a connector case is assembled from a direction of an arrow 3a in FIGS. 3(a) and 3(b).

DESCRIPTION OF EMBODIMENTS

Figure 15:
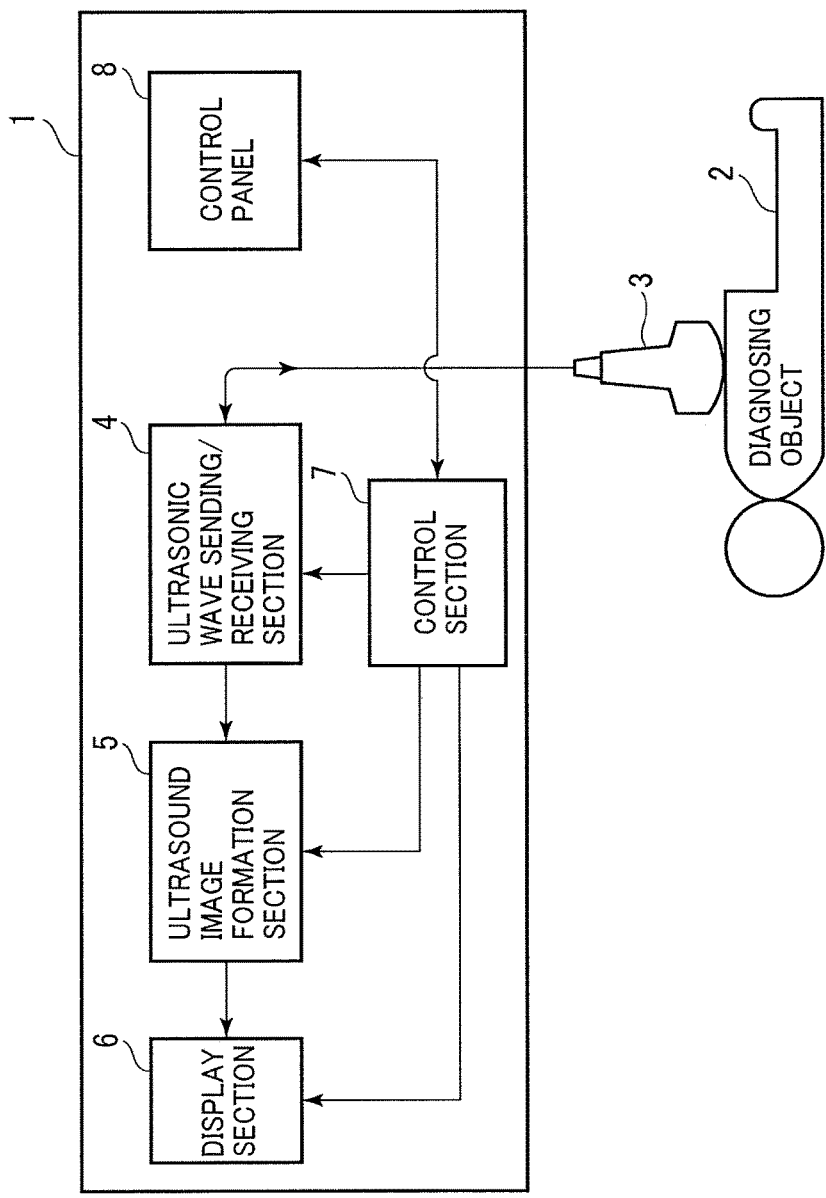
FIG. 15 is a block configuration diagram of an ultrasound diagnostic apparatus including the ultrasound probe of the present invention.

In the following, an ultrasound probe of the present invention is described by reference to the accompanying drawings. FIG. 15 shows a block diagram of one configuration example of an ultrasound diagnostic apparatus including an ultrasound probe 3 of the present invention. The ultrasound probe 3 is configured so as to be attachable and detachable to and from a main body (referred to as an apparatus main body below) 1 of the ultrasound diagnostic apparatus, and in a state attached to the apparatus main body 1, sends ultrasonic waves to an inside of a diagnosing object 2, receives echo signals reflected from a region to be diagnosed in the diagnosing object 2, and sends the received echo signals to the apparatus main body 1 as a sending destination. The apparatus main body 1 includes an ultrasonic wave sending/receiving section 4 configured to send and receive ultrasonic waves to and from the ultrasound probe 3, an ultrasound image formation section 5 configured to form an ultrasound image based on reflected echo signals output from the ultrasonic wave sending/receiving section 4, a display section 6 configured to display the ultrasound image, a control section 7 configured to control these sections, and a control panel 8 configured to give an instruction to the control section 7.

For example, the ultrasonic wave sending/receiving section 4 is adapted to supply wave emission pulses for driving a transducer of the ultrasound probe 3 to the transducer, and receive and process reflected echo signals received by the transducer. The ultrasonic wave sending/receiving section 4 is provided with a sending section configured to supply the wave emission pulses for controlling the driving of the transducer of the ultrasound probe 3, a receiving section configured to receive the reflected echo signals from the inside of the diagnosing object 2, a complex signal conversion section configured to convert the received reflected echo signals to complex signals by quadrature detection, an ultrasonic wave sending/receiving control section configured to control the respective sections, and the like.

For example, the ultrasound image formation section 5 is adapted to generate an ultrasound image by using the complex signals converted in the complex signal conversion section of the ultrasonic wave sending/receiving section 4. That is, the ultrasound image formation section 5 includes an ultrasound image information generation section configured to generate ultrasound image information of a region to be diagnosed by using the complex signals, a digital scan converter section (Digital Scan Converter; referred to as a DSC section below) configured to scan and convert the generated ultrasound image information to a television display image pattern to generate ultrasound image data, a graphic data generation section configured to generate graphic data, such as scales, marks, and characters, supplemented to an image based on the image data obtained by the scan conversion in the DSC section, a synthesis storage section configured to synthesize the ultrasound image data generated in the DSC section and the graphic data generated in the graphic data generation section, and store the obtained data, and an interface used for reading out, from the control section 7, and setting an initial value, a control parameter or the like required for various kinds of processing in the ultrasound image information generation section, the DSC section, the graphic data generation section, and the synthesis storage section.

The display section 6 is adapted to display the ultrasound image formed in the ultrasound image formation section 5, and is composed of, for example, a CRT monitor or a liquid crystal monitor. The control section 7 is adapted to control the operations of the ultrasonic wave sending/receiving section 4, the ultrasound image formation section 5, and the display section 6 based on the instruction input from the control panel 8, and is composed of, for example, a control circuit board.

The ultrasound diagnostic apparatus 1 thereby forms and displays the ultrasound image, such as a two-dimensional ultrasound image, a three-dimensional ultrasound image, or various Doppler images of the region to be diagnosed in the diagnosing object 2.

Figure 1:
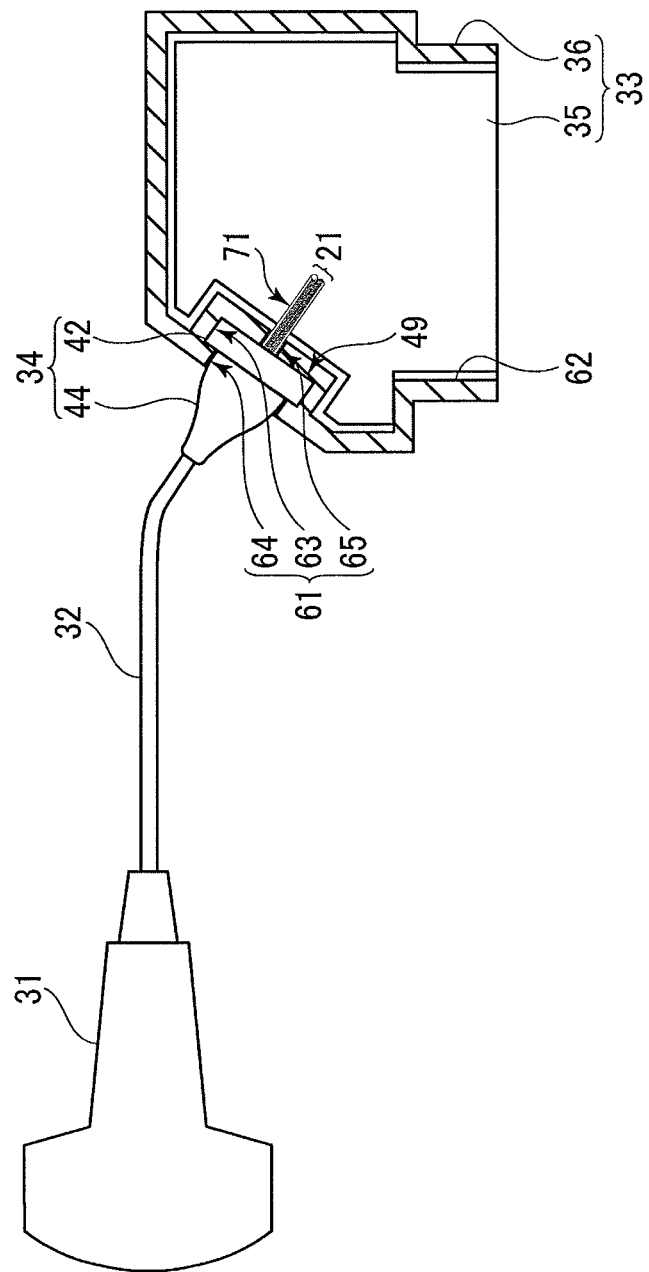
FIG. 1 illustrates an entire configuration of an ultrasound probe of the present invention.

FIG. 1 shows a configuration of the ultrasound probe 3 according to a first embodiment of the present invention, and the ultrasound probe 3 is provided with a main body section 31, a cable 32, a connector section 33, and a bush 34. To be more specific, the ultrasound probe 3 includes the main body section 31 including a plurality of transducers configured to send and receive ultrasonic waves to and from the inside of the diagnosing object 2, the cable 32 including a plurality of signal lines connected to the plurality of transducers and a sheath 22 configured to cover the plurality of signal lines 21, the connector section 33 configured to connect the cable 32 to the ultrasound diagnostic apparatus (the apparatus main body 1), and the bush 34 including a through hole 41 where the cable 32 is passed, and configured to fix the cable 32 passed through the through hole 41 together with the sheath 22 that is folded back, the bush 34 including a fixed portion fixed, in place, to the connector section 33. The cable 32 includes ring members 51 and 52 configured to fix the foldback portion of the sheath 22, and the bush 34 fixes the ring members 51 and 52 by the through hole 41. The details are described later.

The main body section 31 includes the plurality of transducers configured to send ultrasonic waves to the inside of the diagnosing object 2, receive echo signals reflected from the region to be diagnosed in the diagnosing object 2, and send the reflected echo signals to the ultrasonic wave sending/receiving section 4 of the apparatus main body 1 as the sending destination. The plurality of transducers are formed with, for example, a plurality of piezoelectric elements sandwiched between a signal electrode and a ground electrode. A signal line is electrically connected by soldering or the like to the signal electrode, and a ground line is electrically connected by soldering or the like to the ground electrode. The signal line and the ground line are connected to the cable 32 by soldering or a connector board.

Also, the transducers are arranged, for example, for 1 to m channels (m is any integer) in a long-axis direction of the ultrasound probe 3, and focusing of sent/received ultrasonic waves is made in the long-axis direction. Moreover, when the transducers are also cut into k pieces in a short-axis direction and arranged for 1 to k channels (k is any integer), focusing of sent/received ultrasonic waves can be also made in the short-axis direction by varying a delay time given to each of the transducers (1 to k channels) in the short-axis direction. In this case, sent waves are weighted by changing an amplitude of an ultrasonic wave sending signal given to each of the transducers in the short-axis direction, and received waves are weighted by changing an amplification degree or an attenuation degree of an ultrasonic wave received signal from each of the transducers in the short-axis direction. By turning ON and OFF the respective transducers in the short-axis direction, aperture control can be also performed.

Figure 2:
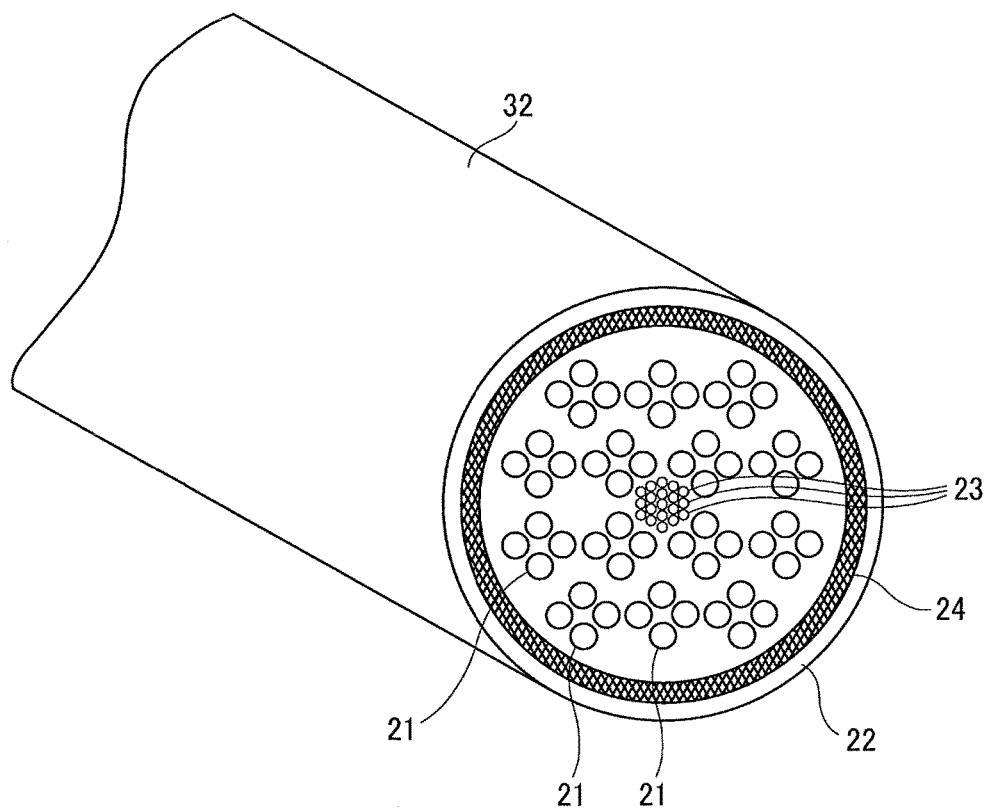
FIG. 2 illustrates a sectional view of an internal configuration of a cable.

FIG. 2 shows a configuration of the cable 32. The cable 32 connects the plurality of transducers as described above to the ultrasonic wave sending/receiving section 4 of the apparatus main body 1 as the sending destination of the reflected echo signals. As shown in FIG. 2, the cable 32 includes the plurality of signal lines 21 configured to send the reflected echo signals to the ultrasonic wave sending/receiving section 4, and the sheath 22 configured to cover the plurality of signal lines 21, and the plurality of signal lines 21 twisted together are covered with the sheath 22. The signal lines 21 are connected to the transducers of the main body section 31, and are provided in number corresponding to the number of the transducers. The cable 32 also includes a plurality of line materials 23 interposed in a space among the plurality of signal lines 21 along the signal lines 21 as a tension member, and a braided shield 24 interposed in a space between the plurality of signal lines 21 and the sheath 22 along the plurality of signal lines 21 and the sheath 22 for blocking signal noise.

While a resin of vinyl chloride, silicone or the like can be used as a material of the sheath 22, the material is not particularly limited as long as the sheath 22 can be folded back as described later. A fibrous material or the like can be used as the line material 23, and FIG. 2 shows one example in which the line materials 23 are interposed in a center portion of the cable 32. Also, as the braided shield 24, a material obtained by braiding metal wires such as copper wires, or thin line materials such as cotton threads in a reticular form may be used. The cable 32 constitutes a so-called coaxial multi-core cable by coaxially arranging the line materials 23 in the center portion, and the signal lines 21, the braided shield 24, and the sheath 22 around the line materials 23.

Figure 3:
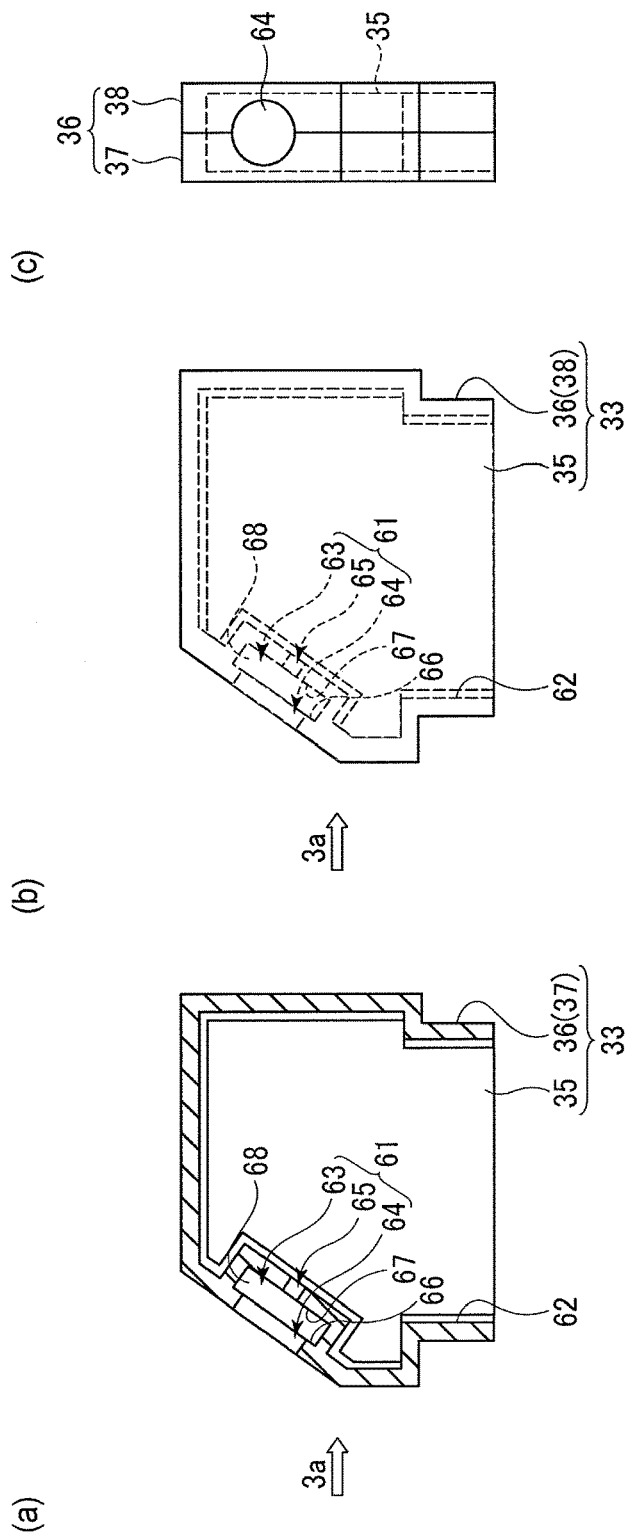
FIG. 3 illustrates a configuration of a connector section.

FIGS. 3(a) to 3(c) show a configuration of the connector section 33. The connector section 33 is an interface member configured to connect the cable 32 to the ultrasonic wave sending/receiving section 4, and includes a connector body 35 and a connector case 36. For example, the connector body 35 is provided with a printed wiring board configured to connect the plurality of signal lines 21 of the cable 32 to the ultrasonic wave sending/receiving section 4, a connection portion of the signal lines 21 connected to the printed wiring board, a sheet metal made of metal configured to block noise, and a ferrite core that is indispensable for EMC (Electro Magnetic Compatibility) measures. The connector body 35 electrically connects the cable 32 to the ultrasonic wave sending/receiving section 4 with a terminal of the printed wiring board joined with a joining target portion of the ultrasonic wave sending/receiving section 4. Since any arrangement may be employed for these members constituting the connector body 35, the arrangement is not particularly limited here.

The connector case 36 is a casing configured to store the bush 34 (FIG. 1) and the connector body 35, and has a structure in which two-divided case constituent bodies 37 and 38 are assembled together to store the bush 34 and the connector body 35 therein. In this case, a bush storage section 61 for storing the bush 34, and a connector body storage section 62 for storing the connector body 35 are provided in the case constituent bodies 37 and 38.

A groove portion 63 where a fixed portion 42 of the bush 34 described below is fitted so as to fix the bush 34, a hole portion 64 configured to bring the groove portion 63 and a connector outer portion into communication, and a hole portion 65 configured to bring the groove portion 63 and the connector body storage section 62 into communication are respectively formed in the bush storage section 61. The groove portion 63 is formed as a groove whose recess portion is continuous in a semi-circumferential shape in each of the case constituent bodies 37 and 38 such that the recess portions where a peripheral edge of the fixed portion 42 is fitted over the entire periphery become circumferentially continuous when the case constituent body 37 and the case constituent body 38 are assembled together.

Accordingly, the groove portion 63 fixes the bush 34 in place, with the fixed portion 42 fitted in a state in which the peripheral edge of the fixed portion 42 is held by wall portions 66 and 67 and a bottom portion 68 forming the groove. Also, the two hole portions 64 and 65 are formed as semi-circular cutouts in the case constituent body 37 and the case constituent body 38 so as to become circular through holes when the case constituent body 37 and the case constituent body 38 are assembled together.

The two case constituent bodies 37 and 38 are assembled together in a state in which the bush 34 is stored in the bush storage section 61 and the connector body 35 is stored in the connector body storage section 62. In this state, the peripheral edge of the fixed portion 42 of the bush 34 is fitted to the groove portion 63, and a portion of a body portion 44 of the bush 34 described below is exposed outside from an opening of the hole portion 64. Also, the connection portion of the signal lines 21 of the cable 32 is pulled out to the connector body storage section 62 from the hole portion 65, and connected to the printed wiring board of the connector body 35 stored in the connector body storage section 62.

A hole diameter of the hole portion 64 in a state in which the two case constituent bodies 37 and 38 are assembled together may be set to be smaller than a maximum diameter dimension of the body portion 44 of the bush 34, and larger than a minimum diameter dimension thereof. Accordingly, when the two case constituent bodies 37 and 38 are assembled together, the body portion 44 of the bush 34 comes into a state sandwiched between the semi-circular cutouts forming the hole portion 64. Also, a hole diameter of the hole portion 65 in a state in which the two case constituent bodies 37 and 38 are assembled together may be set to be larger than a bundle of the signal lines 21, for example, slightly larger than a diameter dimension of the braided shield 24 such that the signal lines 21 of the cable 32 can be pulled out into the connector body storage section 62. A method of fixing the two case constituent bodies 37 and 38 is not particularly limited, and for example, any method such as bonding and screwing may be used.

Figure 4:
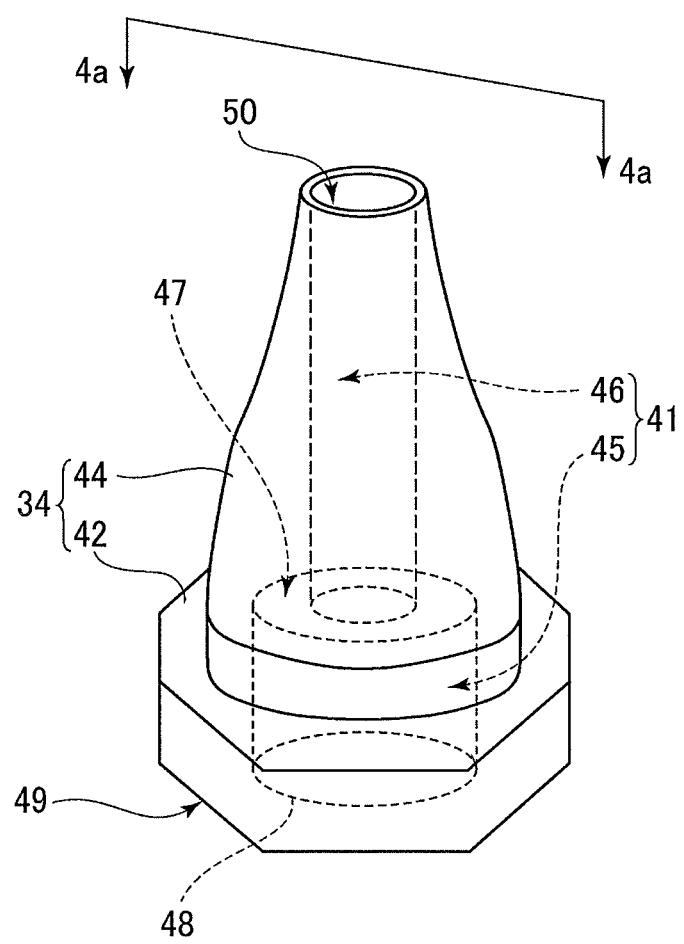
FIG. 4 illustrates a perspective view of a configuration of a bush.
Figure 5:
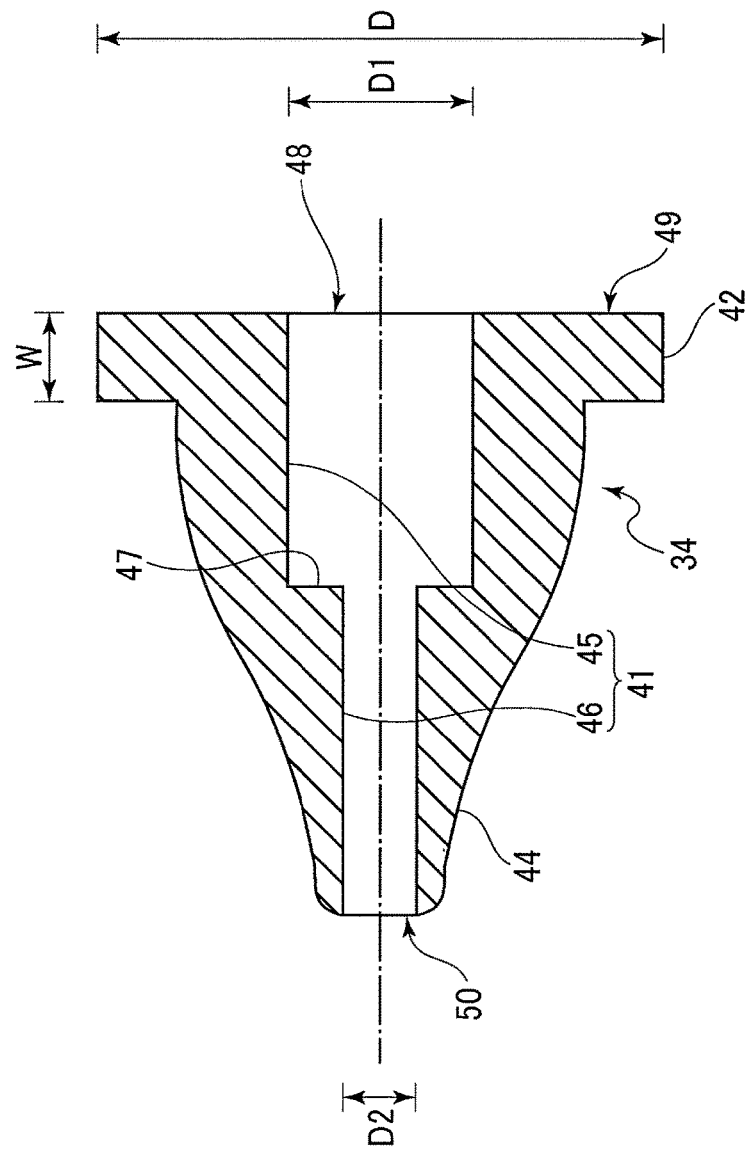
FIG. 5 illustrates a sectional view of the configuration of the bush along an arrow 4a in FIG. 4.

FIGS. 4 and 5 show a configuration of the bush 34. The bush 34 includes the through hole 41 perforated for passing the cable 32, and fixes the cable 32 passed through the through hole 41 to the connector section 33. The bush 34 includes the body portion 44, and the fixed portion 42 to be fixed, in place, to the connector section 33, specifically, the bush storage section 61.

FIGS. 4 and 5 show one example of the configuration of the bush 34 including the plate-like fixed portion 42 that is provided projecting at one side (a right side in FIG. 5) of a perforation direction of the through hole 41 (in other words, an insertion direction of the cable 32), and the bell-like body portion 44 that is gently narrowed toward the other side from the fixed portion 42. In this case, the fixed portion 42 is set such that a maximum dimension D has substantially the same diameter as a groove diameter of the groove portion 63, and a wall thickness dimension W has substantially the same diameter as a width dimension of the groove portion 63 (in other words, an opposite interval between the wall portions 66 and 67) so as to be able to be fitted to the groove portion 63 of the bush storage section 61. FIGS. 4 and 5 show merely one example of an outer shape of the bush 34 (the fixed portion 42 and the body portion 44), and the outer shape of the bush 34 may be set to any shape according to the shape of the connector body storage section 62 or the like as long as the bush 34 is shaped so as to be able to be fixed in place to the connector section 33.

For example, although an end surface 49 of the fixed portion 42 has an octagonal shape in the present embodiment, other polygonal shapes or a circular shape may be also employed. Also, the body portion 44 may be formed in a substantially conical shape. Although a material of the bush 34 is not particularly limited, the bush 34 is preferably made of the same material as the sheath 22 of the cable 32. Therefore, a resin of vinyl chloride, silicone or the like may be used as the material of the bush 34 similarly to the sheath 22.

The through hole 41 of the bush 34 includes a first hole portion 45, and a second hole portion 46 having a smaller hole diameter than the first hole portion 45. The first hole portion 45 is perforated in the fixed portion 42 and one portion of the body portion 44 so as to be coaxial therewith, and the second hole portion 46 is perforated in a remaining portion of the body portion 44 so as to be coaxial with the body portion 44 while communicating with one end portion (a left end portion in FIG. 5) in a perforation direction of the first hole portion 45. Accordingly, the bush 34 has a structure in which the fixed portion 42, the body portion 44, and the through hole 41 (the first hole portion 45 and the second hole portion 46) are coaxially arranged, and the fixed portion 42 and the body portion 44 are penetrated by the through hole 41 (the first hole portion 45 and the second hole portion 46) in the perforation direction to provide openings 48 and 50 on the both sides of the perforation direction.

In the first hole portion 45, a hole diameter D1 thereof is set to a constant dimension having a larger diameter (specifically, an opening diameter of the opening 48) than a first enlarged diameter portion 25 of the cable 32 described below, and a length thereof (a dimension in the perforation direction) is set to be larger than a length (a dimension in a length direction of the cable 32) from the first enlarged diameter portion 25 to a second enlarged diameter portion 26.

That is, the first hole portion 45 is a columnar-shaped hole (a so-called straight hole) where the hole diameter D1 does not change from the opening diameter of the opening 48. However, as long as the first enlarged diameter portion 25 and the second enlarged diameter portion 26 of the cable 32 can be stored in the first hole portion 45 as described later (see FIG. 6), the hole diameter of the first hole portion 45 is not limited to the constant dimension, and for example, may be gradually reduced or enlarged from the opening diameter of the opening 48. In the second hole portion 46, a hole diameter D2 thereof is set to a constant dimension (specifically, an opening diameter of the opening 50) that is substantially the same as a diameter dimension of the cable 32. That is, the second hole portion 46 is a columnar-shaped hole (a so-called straight hole) where the hole diameter D2 does not change from the opening diameter of the opening 50.

As long as the cable 32 can be passed, the hole diameter of the second hole portion 46 is not limited to the constant dimension, and for example, may be gradually reduced or enlarged from the opening diameter of the opening 50. However, in consideration of a configuration in which a hole peripheral surface of the second hole portion 46 and an outer surface of the cable 32 are bonded and fixed together as described later, the hole diameter of the second hole portion 46 preferably has the constant dimension. By employing the configuration in which the through hole 41 includes the first hole portion 45 and the second hole portion 46 as described above, a step is formed in a boundary portion 47 between the first hole portion 45 and the second hole portion 46, and a foldback end portion 54 and the second ring member 52, as the second enlarged diameter portion 26 of the cable 32 described below (see FIG. 6), can be brought into contact and interference with the boundary portion 47.

In the following, the configuration of the cable 32 according to the features of the present embodiment is described by reference to FIG. 6. In the following description, with respect to the length direction, a side where the cable 32 is connected to the transducers of the main body section 31 is referred to as a transducer side (a left side in FIG. 6), and a side where the cable 32 is connected to the ultrasonic wave sending/receiving section 4 of the apparatus main body 1 is referred to as an apparatus main body side (a right side in FIG. 6).

Figure 6:
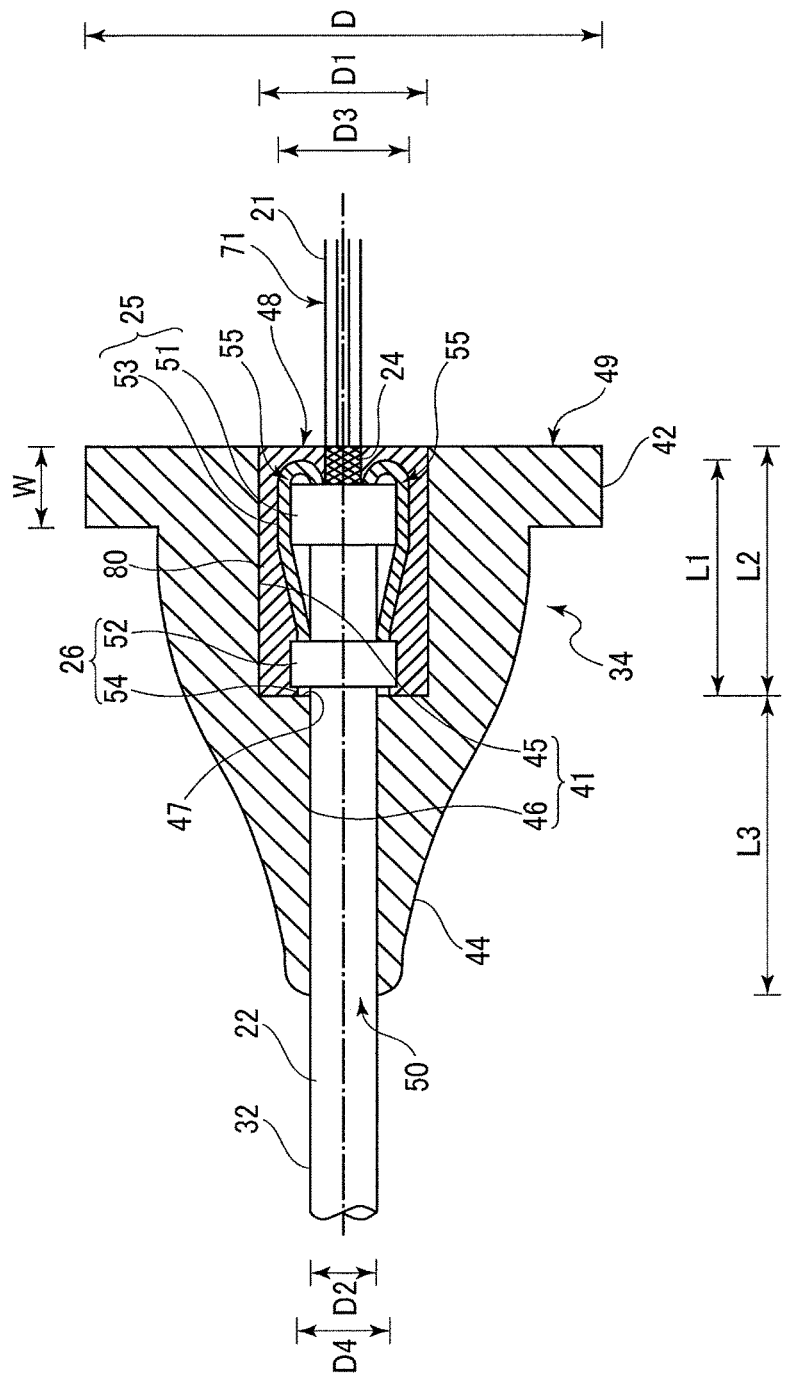
FIG. 6 illustrates a state in which an entire enlarged diameter portion of the cable is integrated with the bush by a binder filling a first hole portion.

FIG. 6 shows a state in which an entire enlarged diameter portion of the cable 32 is integrated with the bush 34 by a binder 80 filling the first hole portion 45. As shown in FIG. 6, the cable 32 includes the first enlarged diameter portion 25 and the second enlarged diameter portion 26 as the enlarged diameter portion. In this case, the second enlarged diameter portion 26 has a larger diameter than the hole diameter of the second hole portion 46 of the bush 34. The first enlarged diameter portion 25 is located closer to the apparatus main body side than the second enlarged diameter portion 26, and has a larger diameter than the second enlarged diameter portion 26.

The first enlarged diameter portion 25 and the second enlarged diameter portion 26 are stored in the first hole portion 45 of the bush 34. That is, as shown in FIG. 6, a maximum diameter dimension D3 of the first enlarged diameter portion 25 and a maximum diameter dimension D4 of the second enlarged diameter portion 26 are set to be smaller than the hole diameter D1 of the first hole portion 45. Also, the length from the first enlarged diameter portion 25 to the second enlarged diameter portion 26 (a dimension L1 in the length direction of the cable 32) is set to be smaller than the length of the first hole portion 45 (a dimension L2 from the opening 48 to the boundary portion 47 with the second hole portion 46). In the following description, the length from the first enlarged diameter portion 25 to the second enlarged diameter portion 26 of the cable 32 is referred to as a cable enlarged diameter length L1, and the length of the first hole portion 45 is referred to as a storage length L2.

In this case, the cable 32 includes the first ring member 51, and the second ring member 52 located closer to the transducer side than the first ring member 51. The sheath 22 of the cable 32 is folded back to the transducer side from a portion where the first ring member 51 is mounted up to an end portion on the apparatus main body side, and a foldback portion 53 covers the first ring member 51. The second ring member 52 is mounted to the foldback end portion 54 on the transducer side of the foldback portion 53 of the sheath 22.

As described above, by mounting the first ring member 51 and the second ring member 52 to the cable 32, the first enlarged diameter portion 25 is composed of the first ring member 51 and the foldback portion 53 of the sheath 22 covering the first ring member 51, and the second enlarged diameter portion 26 is composed of the foldback end portion 54 of the sheath 22 and the second ring member 52.

The first ring member 51 and the second ring member 52 may be set to any thickness within a range in which the first enlarged diameter portion 25 and the second enlarged diameter portion 26 have a larger diameter than the hole diameter D2 of the second hole portion 46 and a smaller diameter than the hole diameter D1 of the first hole portion 45 when the first ring member 51 and the second ring member 52 are mounted to the cable 32. The first ring member 51 and the second ring member 52 may be also set to any width within a range in which the first enlarged diameter portion 25 and the second enlarged diameter portion 26 are stored in the first hole portion 45 (a dimension equal to or less than the storage length L2) without projecting from the opening 48 of the first hole portion 45 when the first ring member 51 and the second ring member 52 are mounted to the cable 32. For example, a metal ring having a larger inner diameter than the diameter dimension of the cable 32, and capable of being reduced in diameter when radially swaged, or a metal band or a bundling band made of resin, capable of being tightened to a predetermined diameter dimension may be employed as the first ring member 51 and the second ring member 52.

Next, the configuration of the first enlarged diameter portion 25 and the second enlarged diameter portion 26 of the cable 32 is described in more detail according to one example of a method of forming the first enlarged diameter portion 25 and the second enlarged diameter portion 26 shown in FIGS. 7 to 13. At this point, the metal ring having a larger inner diameter than the diameter dimension of the cable 32, and capable of being reduced in diameter when radially swaged is used as the first ring member 51 and the second ring member 52 as one example. In FIGS. 7 to 13, an upper side corresponds to the transducer side, and a lower side corresponds to the apparatus main body side.

Figure 7:
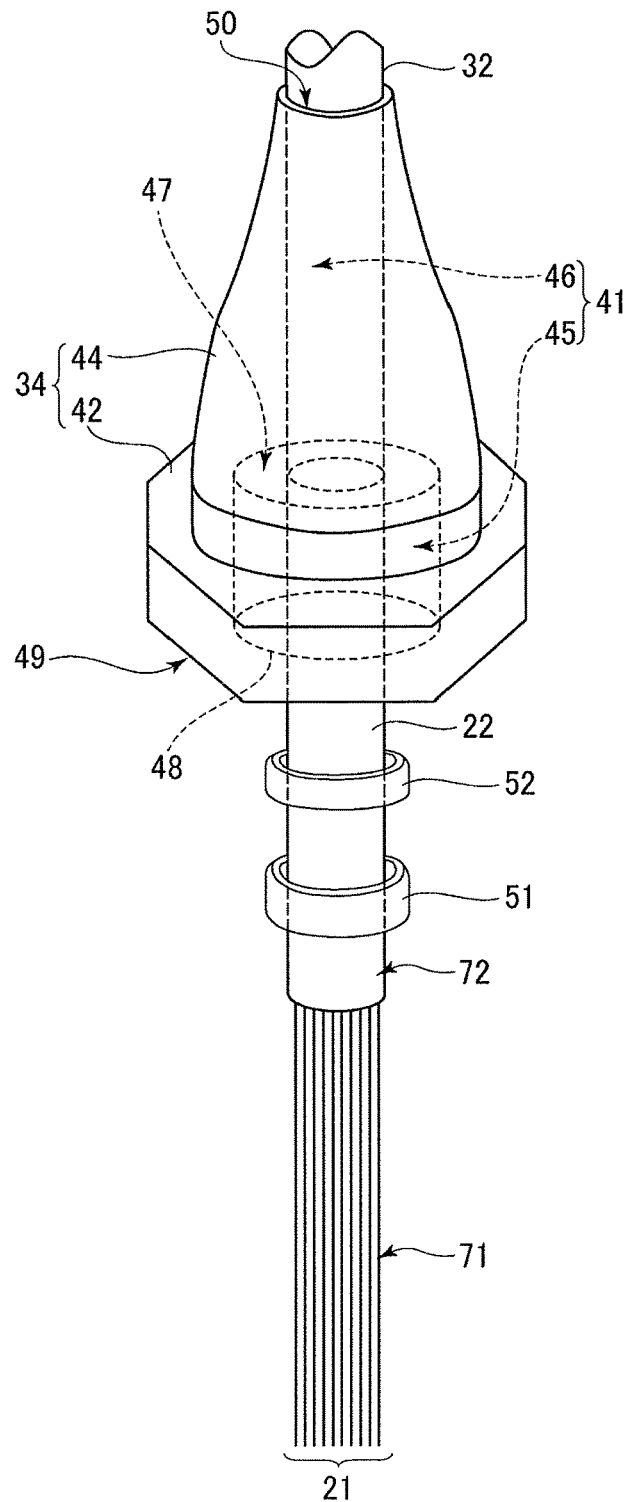
FIG. 7 illustrates a state in which the bush, a second ring member, and a first ring member are inserted through the cable.

When the first enlarged diameter portion 25 and the second enlarged diameter portion 26 are formed, first, the bush 34, the second ring member 52, and the first ring member 51 are inserted through the cable 32. FIG. 7 shows a state in which the bush 34, the second ring member 52, and the first ring member 51 are inserted through the cable 32. At this point, the bush 34, the second ring member 52, and the first ring member 51 are inserted from an end portion 71 on the apparatus main body side of the cable 32 such that these members are arranged in the order of the bush 34, the second ring member 52, and the first ring member 51 from the apparatus main body side to the transducer side of the cable 32, and these members are located closer to the transducer side than an end portion 72 on the apparatus main body side of the sheath 22. The bush 34 is inserted through the cable 32 from the opening 50 into the through hole 41 such that the fixed portion 42 is located on the apparatus main body side, and the body portion 44 is located on the transducer side. In this case, the sheath 22 and the braided shield 24 are removed from the end portion 71 on the apparatus main body side of the cable 32, so that the signal lines 21 come into an uncovered state. The uncovered signal lines 21 are pulled out of the hole portion 65 of the connector case 36 to become the connection portion (see FIG. 1) connected to the printed wiring board of the connector body 35 stored in the connector body storage section 62 when the cable 32 is fixed to the connector section 33 via the bush 34. Although not particularly shown in FIG. 7, the main body section 31 of the ultrasound probe 3 is connected to an end portion on the transducer side of the cable 32 (the same applies to FIGS. 8 to 13).

Figure 8:
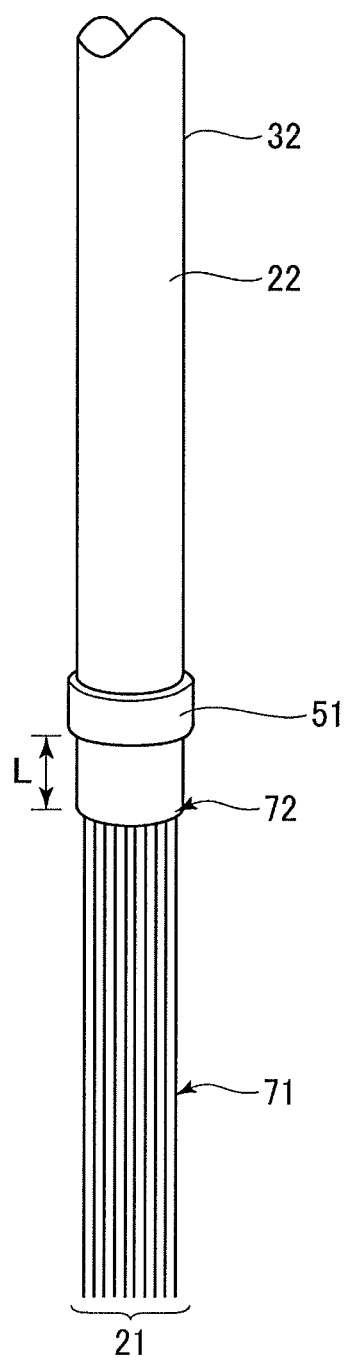
FIG. 8 illustrates a state in which the first ring member is swaged and mounted to the cable.

FIG. 8 shows a state in which the first ring member 51 is mounted to the cable 32 after inserting the bush 34, the second ring member 52, and the first ring member 51 through the cable 32. When the first ring member 51 is mounted to the cable 32, the first ring member 51 is located to the transducer side by a predetermined length L from the end portion 72 on the apparatus main body side of the sheath 22. The length L corresponds to a length of the foldback portion 53 (FIG. 6) of the sheath 22, and is set to be smaller than the length (the storage length L2 (FIG. 6)) of the first hole portion 45 of the bush 34. With the first ring member 51 located as described above, the first ring member 51 is radially swaged by using a predetermined fastener, and thereby reduced in diameter. The first ring member 51 is swaged until the inner diameter of the first ring member 51 becomes substantially the same as the diameter dimension of the cable 32, and the swaged first ring member 51 is fixed to the cable 32 at a swaging position. Although not particularly shown in FIG. 8, the second ring member 52 and the bush 34 inserted through the cable 32 are arranged closer to the transducer side than the first ring member 51 on the cable 32 (the same applies to FIGS. 9 to 11).

Figure 9:
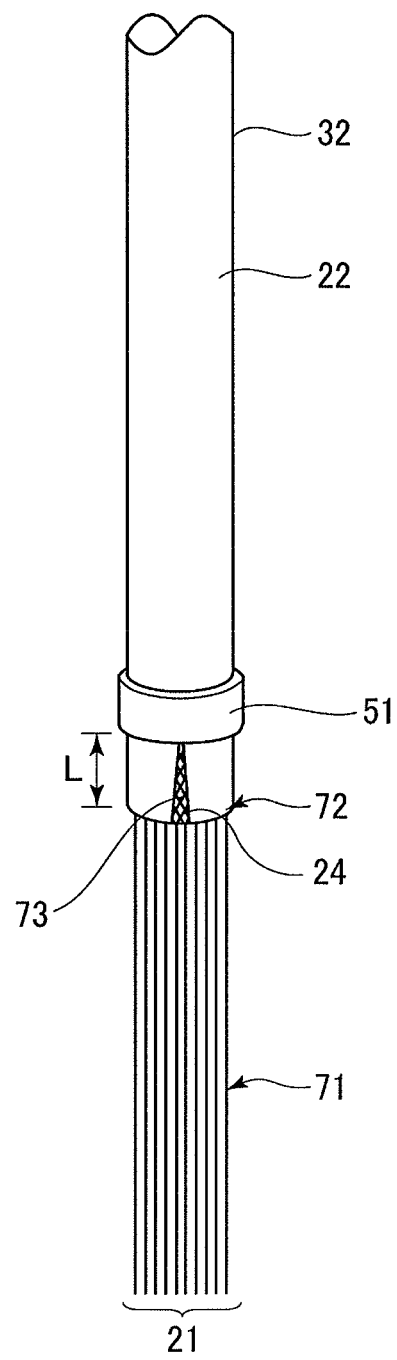
FIG. 9 illustrates a state in which a notch is formed in a sheath.

FIG. 9 shows a state in which a notch 73 is formed in the sheath 22 along the length direction of the cable 32 (a vertical direction in FIG. 9) from the end portion 72 on the apparatus main body side of the sheath 22 up to a mounting portion of the first ring member 51 after mounting the first ring member 51 to the cable 32. In this case, a state in which the sheath 22 is cut out into a triangular shape that is narrowed from the end portion 72 of the sheath 22 to the mounting portion of the first ring member 51, and the notch 73 is formed over the length L is shown as one example. A similar triangular notch is also formed in the sheath 22 on an opposite side from the notch 73 with respect to a circumferential direction (that is, with a phase difference of 180° from the notch 73).

Therefore, two notches 73 are formed in the sheath 22, and two foldback portions 53 (FIG. 6) are formed when the sheath 22 is folded back to the transducer side along the notches 73. The shape of the notch is not limited to the triangular shape as shown in FIG. 9, and for example, the notch (cut) may be formed in a linear shape, or a rectangular shape. The number of the notches is also not particularly limited. That is, the shape and the number of the notches to be formed in the sheath 22 may be set so as to facilitate the foldback operation for folding back the sheath 22 to the transducer side along the notches to form the foldback portions 53. Also, by forming the notches 73 in this manner, the braided shield 24 comes into an exposed state in the portion where the sheath 22 is cut out. Although it is possible to assume that the notches in the sheath 22 is previously formed before mounting the first ring member 51 to the cable 32, the notches are preferably formed after mounting the first ring member 51.

Figure 10:
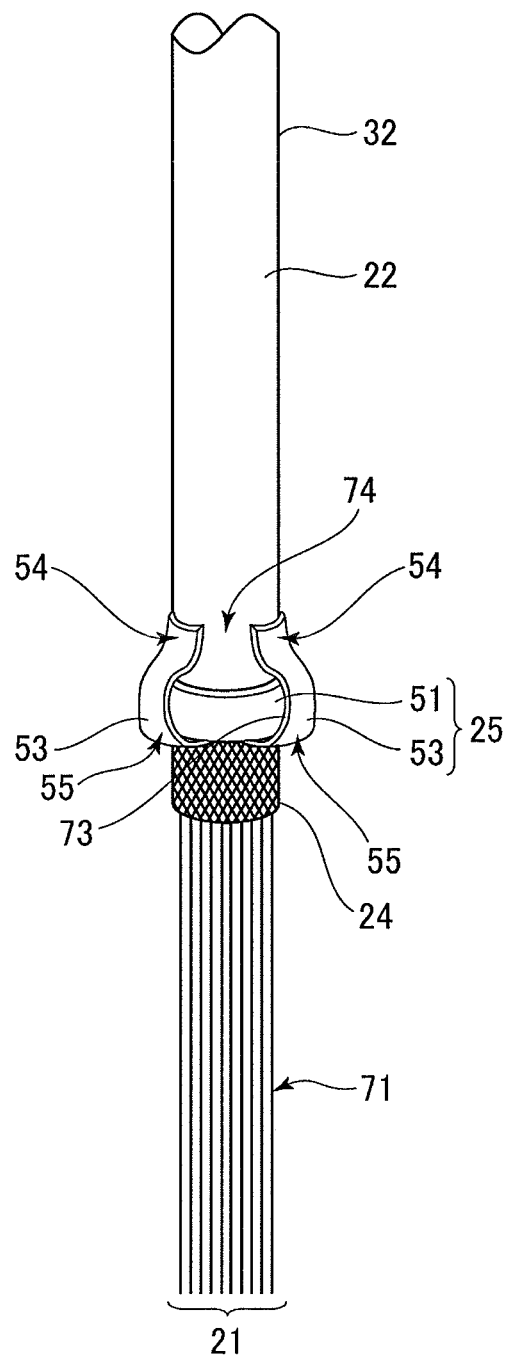
FIG. 10 illustrates a state in which foldback portions are formed by folding back the sheath along the notches, and the first ring member is covered with the foldback portions.

FIG. 10 shows a state in which the foldback portions 53 are formed by folding back the sheath 22 along the notches 73, and the first ring member 51 is covered with the foldback portions 53. As shown in FIG. 10, end portions 55 on the apparatus main body side of the foldback portions 53 are located at substantially the same position as a peripheral edge portion on the apparatus main body side of the first ring member 51 with respect to the length direction of the cable 32 (the vertical direction in FIG. 10).

The end portions (the foldback end portions) 54 on the transducer side of the foldback portions 53 are brought into close contact with an outer surface of the sheath 22. Accordingly, the foldback portions 53 assume a state in which the end portions 55 on the apparatus main body side have a largest diameter dimension and the end portions (the foldback end portions) 54 on the transducer side have a smallest diameter dimension, and are located on the cable 32 in a state in which the diameter dimension is reduced from the end portions 55 to the foldback end portions 54. In this case, since the two notches 73 are formed, the two foldback portions 53 are formed in the sheath 22. The two foldback portions 53 bring the foldback end portions 54 thereof into close contact with the outer surface of the sheath 22 in a state in which the foldback end portions 54 do not contact each other, and a gap 74 according to the notch 73 is formed. The two foldback portions 53 also bring the foldback end portions 54 thereof into close contact with the outer surface of the sheath 22 in a state in which a similar gap is formed on an opposite side from the gap 74 with respect to the circumferential direction. By folding back the sheath 22 as described above, the braided shield 24 comes into an uncovered state in the folded back portion (that is, a portion where the foldback portions 53 cover the cable 32 before being folded back).

Figure 11:
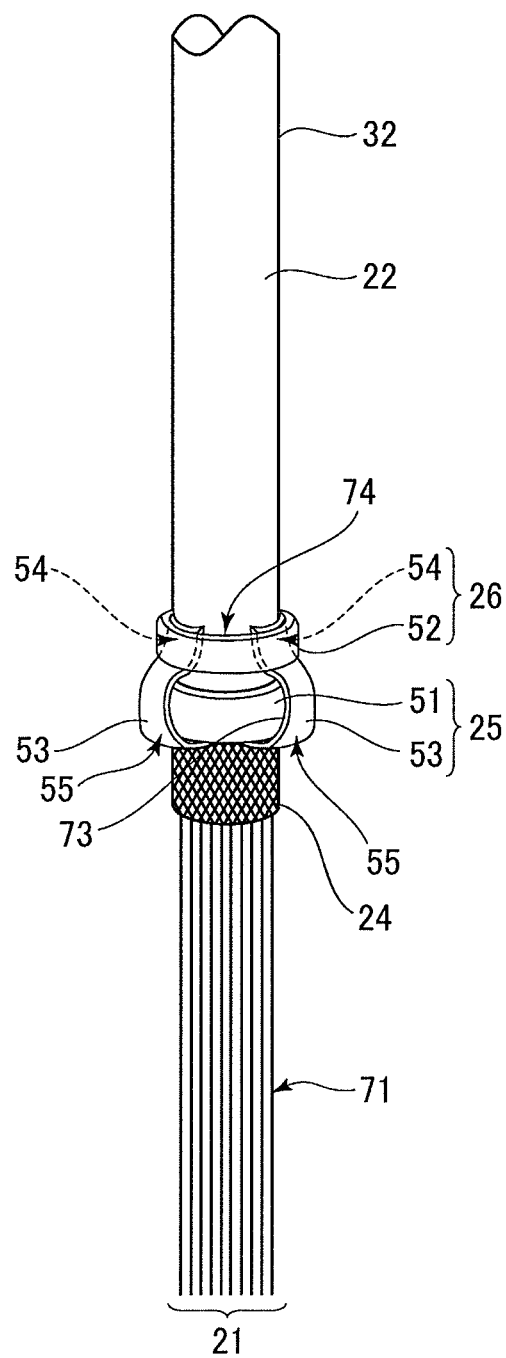
FIG. 11 illustrates a state in which the second ring member is located on foldback end portions of the foldback portions as a mounting position, and swaged.

FIG. 11 shows a state in which the second ring member 52 is mounted to the cable 32 after forming the foldback portions 53 and covering the first ring member 51 with the foldback portions 53. When the second ring member 52 is mounted, the second ring member 52 is moved to the apparatus main body side along the cable 32, and located on the foldback end portions 54 of the foldback portions 53. With the second ring member 52 located as described above, the second ring member 52 is radially swaged by using a predetermined fastener, and thereby reduced in diameter. The second ring member 52 is swaged until the inner diameter of the second ring member 52 becomes substantially the same as the diameter dimension of the foldback end portions 54, and the swaged second ring member 52 is fixed to the cable 32 at a swaging position while holding the foldback end portions 54.

Accordingly, the second ring member 52 is mounted at a position closer to the transducer side than the first ring member 51, and a dimension in the length direction of the cable 32 (the vertical direction in FIG. 11) from the mounting portion of the first ring member 51 to a mounting portion of the second ring member 52 is set to substantially the length of the foldback portions 53, that is, a dimension corresponding to the length L (FIG. 8) from the end portion 72 of the sheath 22 set at the time of mounting the first ring member 51.

By mounting the first ring member 51 and the second ring member 52 to the cable 32 as described above, the first ring member 51 and the foldback portions 53 of the sheath 22 covering the first ring member 51 constitute the first enlarged diameter portion 25 of the cable 32, and the foldback end portions 54 of the sheath 22 and the second ring member 52 constitute the second enlarged diameter portion 26. In this case, the maximum diameter dimension D3 of the first enlarged diameter portion 25 corresponds to the diameter dimension of the foldback portions 53 covering the first ring member 51, and the maximum diameter dimension D4 of the second enlarged diameter portion 26 corresponds to the diameter dimension of the second ring member 52 swaged on the foldback end portions 54 (see FIG. 6). Although not particularly shown in FIG. 11, the bush 34 inserted through the cable 32 is arranged closer to the transducer side than the second ring member 52 on the cable 32.

Figure 12:
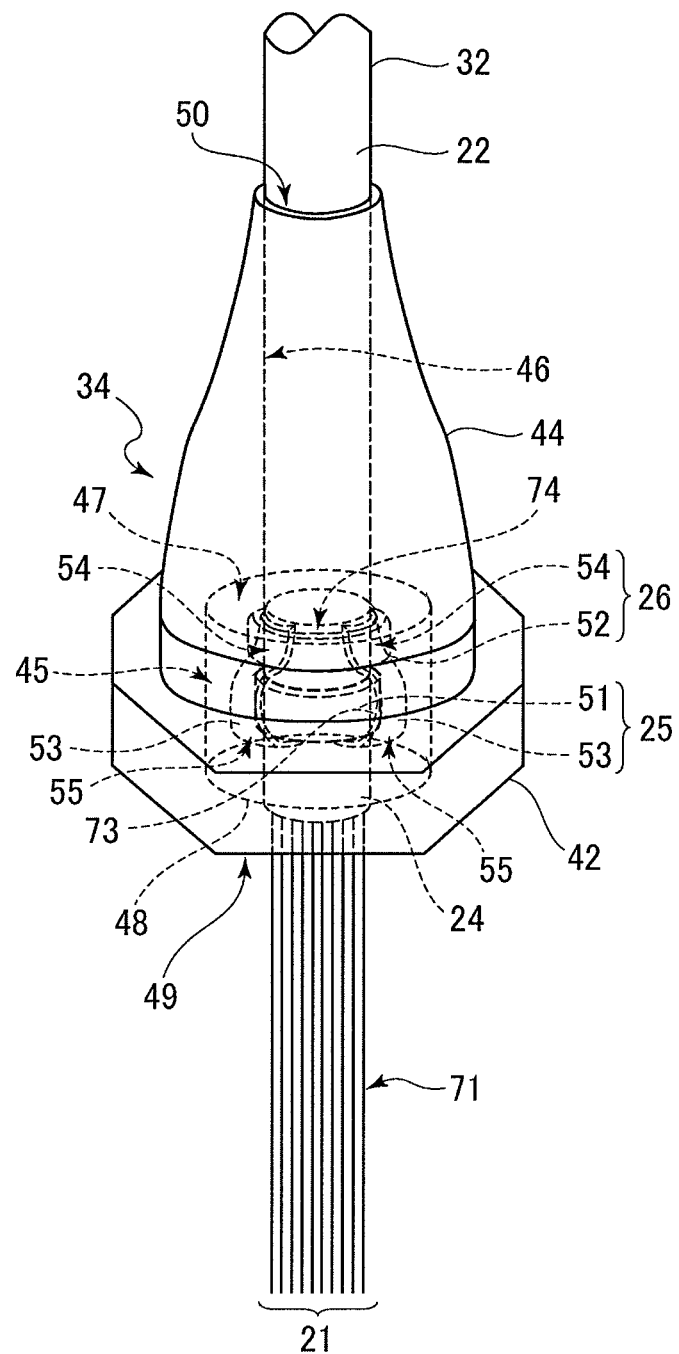
FIG. 12 illustrates a state in which the bush and the cable are fixed together, with the foldback end portions and the second ring member, and the first ring member and the foldback portions being stored in the first hole portion.

FIG. 12 shows a state in which the bush 34 and the cable 32 are fixed together by storing the foldback end portions 54, the second ring member 52, the first ring member 51 and the foldback portions 53 in the first hole portion 45 of the bush 34 after mounting the second ring member 52 to the cable 32 (the foldback end portions 54).

To fix the bush 34 and the cable 32 together, an adhesive is previously applied to the outer surface of the cable 32 on the transducer side from the mounting portion of the second ring member 52 over a range corresponding to a length of the second hole portion 46 of the bush 34 (a dimension L3 from the opening 50 to the boundary portion 47 (FIG. 6)). In this state, the bush 34 is moved to the apparatus main body side along the cable 32 until the foldback end portions 54 and the second ring member 52 come into contact with the boundary portion 47, and the foldback end portions 54, the second ring member 52, the first ring member 51 and the foldback portions 53 are stored in the first hole portion 45. The hole peripheral surface of the second hole portion 46 and the outer surface of the cable 32 may be bonded and fixed together. By confirming that the foldback end portions 54 and the second ring member 52 are in contact and interference with the boundary portion 47, and the bush 34 cannot be moved to the apparatus main body side anymore when the bush 34 is moved, it can be confirmed at the same time that the entire enlarged diameter portion of the cable 32 composed of the first ring member 51, the foldback portions 53, the foldback end portions 54 and the second ring member 52 is completely stored in the first hole portion 45.

Figure 13:
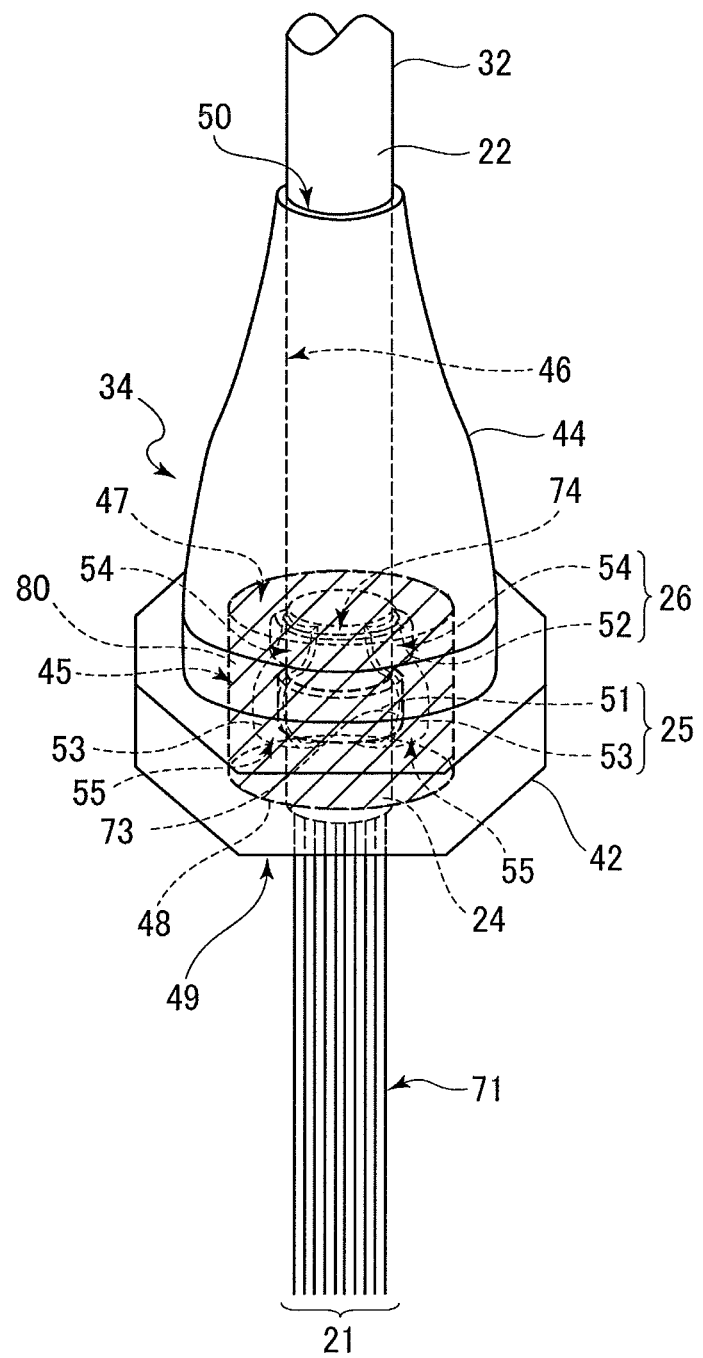
FIG. 13 illustrates a state in which the entire enlarged diameter portion of the cable is integrated with the bush by the binder filling the first hole portion, with the foldback end portions and the second ring member, and the first ring member and the foldback portions being stored in the first hole portion.

FIG. 13 shows a state in which the foldback end portions 54, the second ring member 52, the first ring member 51 and the foldback portions 53 are integrated with the bush 34 by the binder 80 filling the first hole portion 45 after fixing the bush 34 to the cable 32. In this case, the binder 80 is injected into the first hole portion 45 from the opening 48 with the foldback end portions 54, the second ring member 52, the first ring member 51 and the foldback portions 53 stored in the first hole portion 45. The first hole portion 45 is filled with the injected binder 80, and the first ring member 51, the foldback portions 53, the foldback end portions 54 and the second ring member 52 are bound to the first hole portion 45 by the binder 80, and thereby integrated with the bush 34.

Although a material of the binder 80 filling the first hole portion 45 is not particularly limited, the binder 80 is preferably made of the same material as the sheath 22 of the cable 32 and the bush 34. Therefore, a resin of vinyl chloride, silicone or the like may be used as the binder 80 similarly to the sheath 22 and the bush 34. By using the same resin as the sheath 22 and the bush 34 for the binder 80, the binder 80 can be assimilated with the first hole portion 45 of the bush 34 and the foldback portions 53 of the sheath 22, and a bonding strength between the entire enlarged diameter portion of the cable 32 and the bush 34 can be increased. As a result, a tensile stress generated on the cable 32 to the transducer side can be surely applied to the bush 34 and the connector section 33 that fixes the bush 34.

By forming the first enlarged diameter portion 25 and the second enlarged diameter portion 26 as described above, the cable 32 is provided with the enlarged diameter portion, and the entire enlarged diameter portion is integrated with the bush 34 to come into the state shown in FIG. 6. As shown in FIG. 6, since the second enlarged diameter portion 26 composed of the foldback end portions 54 of the sheath 22 and the second ring member 52 has a larger diameter than the hole diameter D2 of the second hole portion 46 of the bush 34 (D2<D4), the foldback end portions 54 and the second ring member 52 as the second enlarged diameter portion 26 can be brought into interference with the boundary portion 47 between the first hole portion 45 and the second hole portion 46 even when the tensile stress to the transducer side is generated on the cable 32. Therefore, the tensile stress can be dispersedly applied to the foldback end portions 54, the second ring member 52, and the boundary portion 47.

Also, the first enlarged diameter portion 25 composed of the first ring member 51 and the foldback portions 53 of the sheath 22 covering the first ring member 51 has a still larger diameter than the second enlarged diameter portion 26 having a larger diameter than the hole diameter of the second hole portion 46 (D2<D4<D3). Therefore, even if a problem occurs in which the tensile stress to the transducer side on the cable 32 cannot be applied to the foldback end portions 54, the second ring member 52, and the boundary portion 47, the tensile stress can be surely applied by causing the first ring member 51 and the foldback portions 53 to interfere with the boundary portion 47. In addition, since the foldback portions 53 of the first enlarged diameter portion 25 is located in the second hole portion 46 in a state in which the diameter dimension is reduced from the end portions 55 on the apparatus main body side to the end portions (the foldback end portions 54) on the transducer side, the foldback portions 53 assume a so-called wedge-like state against the second hole portion 46. Accordingly, the first enlarged diameter portion 25 not only enables the tensile stress to be surely applied, but can also prevent the cable 32 from falling out of the bush 34.

Moreover, since the entire enlarged diameter portion of the cable 32 composed of the first ring member 51, the foldback portions 53, the foldback end portions 54 and the second ring member 52 is integrated with the bush 34 by the binder 80, and the bush 34 is rigidly fixed to the connector section 33, the tensile stress to the transducer side generated on the cable 32 can be also applied to the bush 34 and the connector section 33.

In addition, as shown in FIG. 6, the maximum diameter dimensions D3 and D4 of the first enlarged diameter portion 25 and the second enlarged diameter portion 26 are set to be smaller than the hole diameter D1 of the first hole portion 45, and the length from the first enlarged diameter portion 25 to the second enlarged diameter portion 26 (the cable enlarged diameter length L1) is set to be smaller than the length of the first hole portion 45 (the storage length L2). Thus, the entire enlarged diameter portion of the cable 32 composed of the first ring member 51 and the foldback portions 53, and the foldback end portions 54 and the second ring member 52 can be completely stored in the first hole portion 45. Therefore, the first ring member 51 and the end portions 55 on the apparatus main body side of the foldback portions 53 do not project from the opening 48 of the first hole portion 45.

That is, even when the entire enlarged diameter portion of the cable 32 is completely stored in the first hole portion 45, the entire enlarged diameter portion can be bound by making the binder 80 filling the first hole portion 45 flush with the end surface 49 of the fixed portion 42. Therefore, even when the entire enlarged diameter portion of the cable 32 is integrated with the bush 34, the size and shape of the bush 34 are not changed at all.

As described above, in accordance with the ultrasound probe 3 according to the present embodiment, space saving of a space for fixing the cable 32 and improvement of a tensile strength of the cable 32 can be achieved. As a result, as shown in FIG. 1, the bush storage section 61 serving as the space for fixing the cable 32 can be made smaller as compared to the connector body storage section 62, and a large space can be ensured for the connector body storage section 62. As a result, the connector section 33 can be reduced in size and weight.

As shown in FIG. 2, the plurality of line materials 23 interposed in the space among the plurality of signal lines 21 along the signal lines 21 are provided as the tension member in the cable 32.

Therefore, the line materials 23 may be also used for improving the tensile strength of the cable 32. An embodiment of the ultrasound probe 3 in which the line materials 23 are used for improving the tensile strength of the cable 32 is described below as a second embodiment of the present invention. In the second embodiment, a basic configuration of the ultrasound probe 3 is the same as the above first embodiment except that the line materials 23 are used for improving the tensile strength of the cable 32, and only a configuration specific to the second embodiment is described below. Here, the same constituent members as those of the first embodiment are assigned the same reference numerals in the drawings, and the description is omitted.

Figure 14:
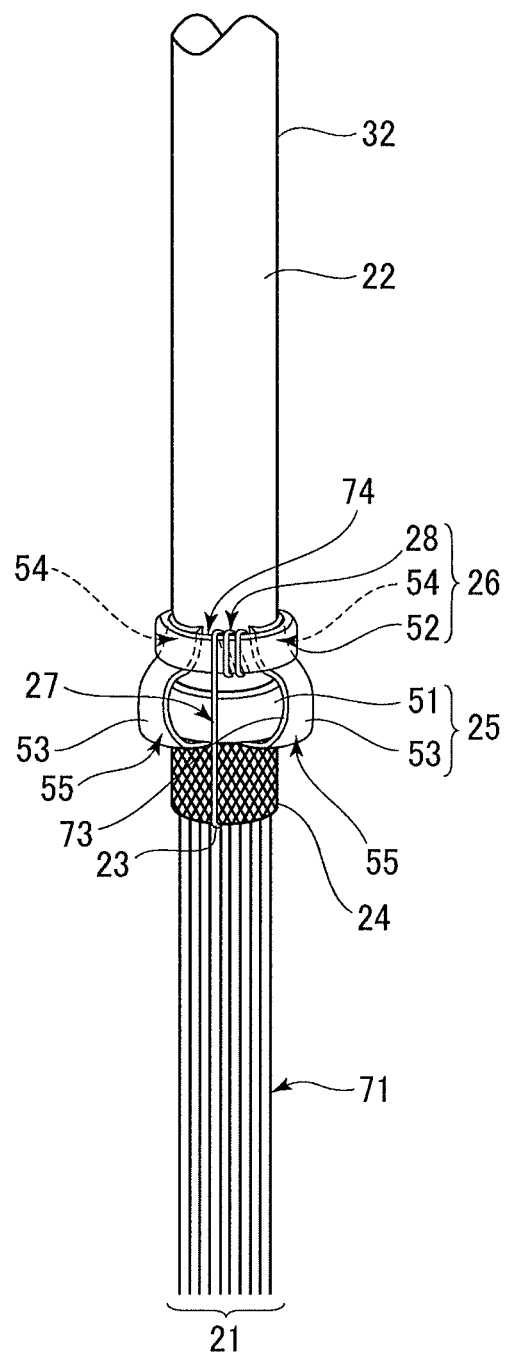
FIG. 14 illustrates a state in which the second ring member around which line materials are wound is mounted.

As shown in FIG. 14, in the present embodiment, the second ring member 52 is mounted to the cable 32 with the line materials 23 wound around the second ring member 52.

In this case, after forming the foldback portions 53 and covering the first ring member 51 with the foldback portions 53, the line materials 23 are pulled outside from a space of the signal lines 21 in an uncovered state at the end portion 71 on the apparatus main body side (the lower side in FIG. 14) of the cable 32. Only some of the plurality of line materials 23 interposed in the center portion of the cable 32 may be pulled outside, or all of the plurality of line materials 23 may be pulled outside. Also, the pulled-out line materials 23 may be used in a twisted manner.

The pulled-out line materials 23 are placed along the braided shield 24 in an uncovered state by forming the foldback portions 53, and bent to the transducer side (the upper side in FIG. 14) along the notch 73, to thereby form a bent portion 27. In this state, the second ring member 52 is moved to the apparatus main body side along the cable 32, and located on the foldback end portions 54 of the foldback portions 53.

The bent portion 27 of the line materials 23 is wound around the second ring member 52 in a state in which the second ring member 52 is located as described above. A winding position and the number of windings are adjusted by adjusting the length of the bent portion 27 such that a wound portion 28 of the line materials 23 is stored in the gap 74 formed between the two foldback portions 53 when the line materials 23 are wound. Since the similar gap is formed between the two foldback portions 53 on the opposite side from the gap 74 with respect to the circumferential direction, the line materials 23 are also wound around the second ring member 52 at the gap position, to provide a similar wound portion. At this point, the pulled-put line materials 23 may be divided into two portions, bent, and wound around the second ring member 52.

The second ring member 52 is radially swaged by using a predetermined fastener, and thereby reduced in diameter in a state in which the line materials 23 are wound around the second ring member 52 as described above. The second ring member 52 may be swaged until the inner diameter of the second ring member 52 becomes substantially the same as the diameter dimension of the foldback end portions 54, and the swaged second ring member 52 may be fixed to the cable 32 at a swaging position while holding the foldback end portions 54 and bringing the wound portions 28 of the line materials 23 into close contact with the sheath 22.

Accordingly, the wound portions 28 of the line materials 23 constitute the second enlarged diameter portion 26 together with the foldback end portions 54 of the sheath 22 and the second ring member 52. Therefore, in the present embodiment, since the wound portions 28 of the line materials 23 project in a diameter enlarging direction beyond the second ring member 52, the diameter of the second enlarged diameter portion 26 is increased by an amount corresponding to a diameter dimension of the wound portions 28. However, the maximum diameter dimension of the second enlarged diameter portion 26 composed of the foldback end portions 54, the second ring member 52, and the wound portions 28 of the line materials 23 is set so as not to be larger than the maximum diameter dimension of the first enlarged diameter portion 25.

As described above, in accordance with the present embodiment, since the second enlarged diameter portion 26 composed of the foldback end portions 54 of the sheath 22, the second ring member 52, and also the wound portions 28 of the line materials 23 has a still larger diameter than the hole diameter D2 of the second hole portion 46 of the bush 34 (FIG. 6), the foldback end portions 54, the second ring member 52, and the wound portions 28 of the line materials 23 as the second enlarged diameter portion 26 can be brought into interference with the boundary portion 47 between the first hole portion 45 and the second hole portion 46 even when the tensile stress to the transducer side is generated on the cable 32. Therefore, the tensile stress can be dispersedly applied to the wound portions 28 of the line materials 23 in addition to the foldback end portions 54, the second ring member 52, and the boundary portion 47. As a result, the tensile strength of the cable 32 can be further improved.

It should be noted that the line materials 23 are interposed in the cable 32 as the tension member, and the line materials 23 are utilized as one constituent element of the second enlarged diameter portion 26 in the present embodiment. Therefore, a change in the configuration of the cable 32 is not required, and a cost increase is not particularly caused. However, it is also possible to assume that a metal wire or the like to be wound around the second ring member 52 is prepared separately from the line materials 23, and the metal wire is wound around the second ring member 52.

Although the convex-shaped ultrasound probe 3 in which the plurality of transducers are arranged in a convex arc shape is assumed as one example in the first embodiment and the second embodiment described above, the ultrasound probe according to the present invention may have a liner shape in which the transducers are arranged linearly or in a planar shape, or a body cavity probe, a transesophageal probe, or the like may be also employed. The present invention may be also applied to an ultrasound endoscope including an optical endoscope and an ultrasound probe.

Moreover, although the case in which the present invention is applied to the hand-carry type ultrasound diagnostic apparatus is assumed as one example in the first embodiment and the second embodiment, such advantages that the degree of handling freedom of the ultrasound probe can be improved or the like are also provided in a cart-type ultrasound diagnostic apparatus by reducing the size and weight of the connector section, and the present invention can be applied to any type of the ultrasound diagnostic apparatus.

The ultrasound probe cable may be defined as one including the cable 32 including the plurality of signal lines 21 connected to the plurality of transducers and the sheath 22 configured to cover the plurality of signal lines 21, and the bush 34 including the fixed portion fixed, in place, to the connector section 33.

Therefore, in accordance with the first embodiment and the second embodiment, the ultrasound probe cable includes the plurality of signal lines 21 connected to the plurality of transducers, the sheath 22 configured to cover the plurality of signal lines 21, and the bush 34 including the through hole for the cable where the plurality of signal lines 21 are passed, and configured to fix the plurality of signal lines 21 passed through the through hole for the cable together with the sheath 22 that is folded back. The ultrasound probe cable includes the ring member 52 configured to fix the foldback portion of the sheath 22, and the bush 34 fixes the ring member 52 by the through hole 41. The other features of the ultrasound probe cable are the same as those of the first embodiment and the second embodiment.

REFERENCE SIGNS LIST

3 Ultrasound Probe
21 Signal Line
22 Sheath
25 First Enlarged Diameter Portion
26 Second Enlarged Diameter Portion
31 Main Body Section
32 Cable
33 Connector Section
34 Bush
41 Through Hole
42 Fixed Portion
45 First Hole Portion
46 Second Hole Portion
D2 Hole Diameter of the Second Hole Portion

The invention claimed is:
1. An ultrasound probe comprising:
a main body section including a plurality of transducers configured to send and receive an ultrasonic wave to and from an inside of a diagnosing object;
a cable including a plurality of signal lines connected to the plurality of transducers, and a sheath configured to cover the plurality of signal lines;
a connector section configured to connect the cable to an ultrasound diagnostic apparatus; and
a bush including a through hole where the cable is passed, configured to fix the cable passed through the through hole together with the sheath that is folded back, and including a fixed portion fixed, in place, to the connector section, wherein
the through hole includes a first hole portion, and a second hole portion having a smaller hole diameter than the first hole portion,
the cable includes a first enlarged diameter portion and a second enlarged diameter portion, the second enlarged diameter portion has a larger diameter than the hole diameter of the second hole portion, the first enlarged diameter portion is located closer to a connection side with the ultrasound diagnostic apparatus than the second enlarged diameter portion, and has a larger diameter than the second enlarged diameter portion, and the first enlarged diameter portion and the second enlarged diameter portion are stored in the first hole portion.

2. The ultrasound probe according to claim 1, wherein the cable includes a ring member configured to fix the foldback portion of the sheath, and the bush fixes the ring member by the through hole.

3. The ultrasound probe according to claim 1, wherein the cable includes a first ring member, and a second ring member located closer to a connection side with the transducers than the first ring member, the sheath is folded back to the connection side with the transducers from a portion where the first ring member is mounted up to an end portion on the connection side with the ultrasound diagnostic apparatus, and the foldback portion covers the first ring member, the second ring member is mounted to a foldback end portion on the connection side with the transducers of the foldback portion of the sheath, the first enlarged diameter portion has the first ring member and the foldback portion of the sheath covering the first ring member, and the second enlarged diameter portion has the foldback end portion of the sheath and the second ring member.

4. The ultrasound probe according to claim 3, wherein the cable includes a plurality of line materials interposed in a space among the plurality of signal lines along the plurality of signal lines as a tension member, and the line materials are bent to the connection side with the transducers from the mounting portion of the first ring member up to the end portion on the connection side with the ultrasound diagnostic apparatus to form a bent portion, and the bent portion is wound around the second ring member.

5. The ultrasound probe according to claim 3, wherein the first ring member and the second ring member are metal rings whose inner diameter can be reduced by swaging, and the metal rings are mounted to the cable by reducing the inner diameter by swaging.

6. The ultrasound probe according to claim 1, wherein the second enlarged diameter portion contacts a boundary portion between the first hole portion and the second hole portion.

7. The ultrasound probe according to claim 1, wherein the cable and the bush are fixed together by an adhesive applied to the second hole portion.

8. The ultrasound probe according to claim 1, wherein the first hole portion is filled with a binder in a state in which the first enlarged diameter portion and the second enlarged diameter portion are stored in the first hole portion.

9. The ultrasound probe according to claim 1, wherein the bush and the sheath are made of a same material.

10. The ultrasound probe according to claim 8, wherein the binder is made of the same material as the bush and the sheath.

11. An ultrasound probe cable comprising:

a plurality of signal lines connected to a plurality of transducers;

a sheath configured to cover the plurality of signal lines; and a bush including a through hole where the plurality of signal lines are passed, and configured to fix the plurality of signal lines passed through the through hole together with the sheath that is folded back, wherein the through hole includes a first hole portion, and a second hole portion having a smaller hole diameter than the first hole portion, the plurality of signal includes a first enlarged diameter portion and a second enlarged diameter portion, the second enlarged diameter portion has a larger diameter than the hole diameter of the second hole portion, the first enlarged diameter portion is located closer to a connection side with an ultrasound diagnostic apparatus than the second enlarged diameter portion, and has a larger diameter than the second enlarged diameter portion, and the first enlarged diameter portion and the second enlarged diameter portion are stored in the first hole portion.

12. The ultrasound probe cable according to claim 11, further comprising a ring member configured to fix the foldback portion of the sheath, wherein the bush fixes the ring member by the through hole.

* * * * *